United States Patent
Bigelow, Jr. et al.

(10) Patent No.: US 7,025,062 B2
(45) Date of Patent: Apr. 11, 2006

(54) CONVERTIBLE HEAD GEAR SLING DEVICE

(76) Inventors: Floyd E. Bigelow, Jr., 18003 Spellbrook, Houston, TX (US) 77084; Elizabeth K. Bigelow, 18003 Spellbrook, Houston, TX (US) 77084

( * ) Notice: Subject to any disclaimer, the term of this patent is extended or adjusted under 35 U.S.C. 154(b) by 74 days.

(21) Appl. No.: 10/350,546

(22) Filed: Jan. 23, 2003

(65) Prior Publication Data

US 2004/0147860 A1 Jul. 29, 2004

(51) Int. Cl.
*A61F 5/37* (2006.01)

(52) U.S. Cl. .................. 128/876; 602/17; 128/DIG. 15

(58) Field of Classification Search ................ 128/846, 128/848, 869, 876, DIG. 15; 602/17; 2/DIG. 6
See application file for complete search history.

(56) References Cited

U.S. PATENT DOCUMENTS

| 688,163 | A | | 12/1901 | Fields |
| 3,570,495 | A | * | 3/1971 | Wright ................ 128/DIG. 15 |
| 3,724,470 | A | | 4/1973 | Wilson ...................... 132/46 R |
| 4,190,054 | A | | 2/1980 | Brennan ...................... 128/402 |
| 4,215,687 | A | * | 8/1980 | Shaw ......................... 128/169 |
| 4,394,782 | A | | 7/1983 | Wasson ......................... 2/181 |
| 4,915,096 | A | * | 4/1990 | Winstone ............. 128/DIG. 15 |
| 4,926,848 | A | | 5/1990 | Shimkus et al. ............ 128/169 |
| 4,939,818 | A | * | 7/1990 | Hahn |
| 5,015,251 | A | * | 5/1991 | Cherubini ............ 128/DIG. 15 |
| 5,076,288 | A | * | 12/1991 | Millard et al. ............... 128/869 |
| 5,120,300 | A | | 6/1992 | Shaw .......................... 602/61 |
| 5,361,416 | A | | 11/1994 | Petrie et al. ................. 2/171.2 |
| 5,377,360 | A | | 1/1995 | Fleitman ........................ 2/181 |
| 5,687,743 | A | | 11/1997 | Goodwin .................... 128/848 |
| 5,787,894 | A | | 8/1998 | Holt ........................... 128/848 |
| 5,822,798 | A | | 10/1998 | Boxley ....................... 2/182.6 |
| 5,944,029 | A | | 8/1999 | Brenner ...................... 132/247 |
| D415,837 | S | | 10/1999 | Williams .................. D24/193 |
| 6,449,816 | B1 | | 9/2002 | Dudek et al. ................. 24/306 |

* cited by examiner

*Primary Examiner*—Michael A. Brown
(74) *Attorney, Agent, or Firm*—Guy McClung

(57) ABSTRACT

A device for releasably emplacement around a part of a person's body, the device having at least one body member having a length and a width and two spaced-apart ends including a first end and a second end and a top side and a bottom side, a first amount of releasably cooperating fastener material on the first end on the top side of the at least one body member, a second amount of releasably cooperating fastener material on the second end on the top side of the at least one body member, a third amount of releasably cooperating fastener material on the first end on the bottom side of the at least one body member, a fourth amount of releasably cooperating fastener material on the second end on the bottom side of the at least one body member, and the amounts of releasably cooperating fastener material positioned so that the first amount can releasably cooperate with the fourth amount upon folding the body member so that the ends are adjacent each other and the second amount can releasbly cooperate with the third amount upon folding the body member so that the ends are adjacent each other.

14 Claims, 2 Drawing Sheets

CONVERTIBLE HEAD GEAR SLING DEVICE

BACKGROUND OF THE INVENTION

1. Field of the Invention

The present invention is directed to devices for maintaining an animal's or person's mouth relatively shut and to sling, devices used to support and/or hold an animal's limb or a person's arm.

2. Description of Related Art

The prior art discloses a wide variety of head gear for maintaining a person's head and mouth in a certain position. Certain prior art devices are useful while a person sleeps.

The prior art discloses a wide variety of sling devices for supporting an injured or broken limb, arm or hand.

There has long been a need, recognized by the present inventors, for an easily manipulable head gear device which can hold a person's mouth shut, particularly during sleep, without excessive binding and without slipping off the person's head; and a need for such a device which is also convertible for use as a sling.

SUMMARY OF THE PRESENT INVENTION

The present invention, in certain aspects, provides a head gear device which can be easily emplaced around an animal's or person's head and chin to maintain the mouth closed, particularly during sleep. The device has a body with areas of releasably cooperating fastener material which make it possible to easily wrap the body around a person's head and chin and affix it in place.

By appropriately locating a relatively softer type of one form of the releasably cooperating fastener material, in certain embodiments, a cushion or pad is provided against a person's chin. By appropriately locating an area of the releasably cooperating fastener material on the body in certain embodiments. The material cooperates with a person's hair to maintain a correct position of the device, even during sleep.

In certain embodiments a head gear device according to the present invention has a body with two sides and two ends and amounts of releasably cooperating fastener material are at both ends on each side of the body so that either side of the body can be against a person's skin. This also insures that a softer area of the releasably cooperating fastener material will always be positionable beneath a person's chin. Similarly, amounts of releasably cooperating fastener material are, in certain aspects, located on the body so that one such area is always available for positioning against a person's hair to provide stability and to help maintain a desired position of the device with respect to a person's head and chin. In other aspects an amount of padding or cushioning material is located for positioning over a person's hair. In one aspect both padding/cushioning material is located for positioning adjacent a person's hair and releasably cooperating fastener material for cooperating with some of the hair to maintain the device's position. Use of such a head gear device during sleep can inhibit the user's snoring, tongue biting, and/or lip biting, inside-of-check biting, and/or grinding of teeth.

In one aspect dual devices as described above are interconnected so that one device is releasably emplaceable around a person's neck and the other is releasably emplaceable around a person's forearm to provide a sling for the arm. Suitable amounts of padding or cushioning material may be located on the device as desired, e.g. to provide a cushion between part of the arm and the device or part of a person's neck and the device.

In certain aspects padding or cushioning material is itself releasably connected to a device according to the present invention with releasably cooperating fastener material material.

It is, therefore, an object of at least certain preferred embodiments of the present invention to provide:

New, useful, unique, efficient, non-obvious devices for maintaining a person's or an animal's mouth in a closed position, particularly when the person or animal is unconscious or asleep;

Such devices which are easily emplaceable around a person's or animal's head and chin and removable therefrom;

Such devices with one or more cushion areas positionable adjacent a person's or animal's chin, ear, etc.;

Such a device with an area of releasably cooperating fastener material for cooperating with a person's or animal's hair to maintain the device in a desired position with respect to a person's or animal's head and chin; and Such a device which, when used with another such device, provides a sling for supporting a person's arm or a limb of an animal.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of certain embodiments of the invention may be had by references to the embodiments which are shown in the drawings which form a part of this specification.

DESCRIPTION OF EMBODIMENTS PREFERRED AT THE TIME OF FILING FOR THIS PATENT

Figure 1A:
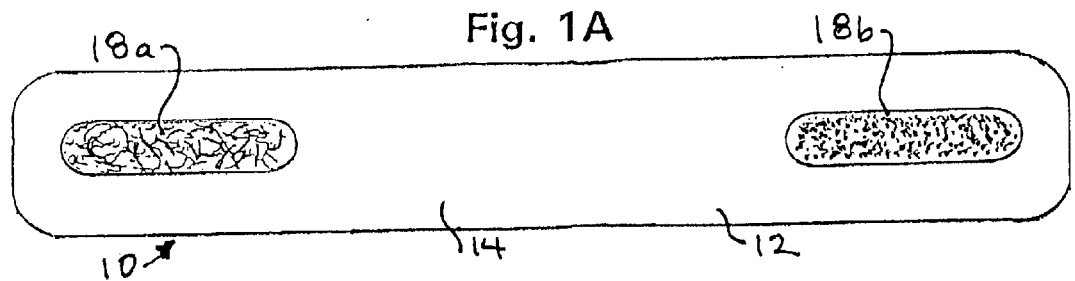
FIG. 1A is a top view of a device according to the present invention.
Figure 1B:
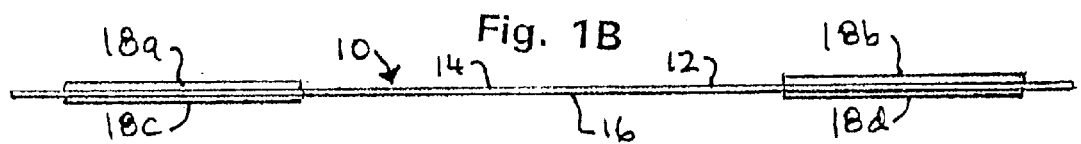
FIG. 1B is a side view of the device of FIG. 1A.
Figures 1C, 1D:
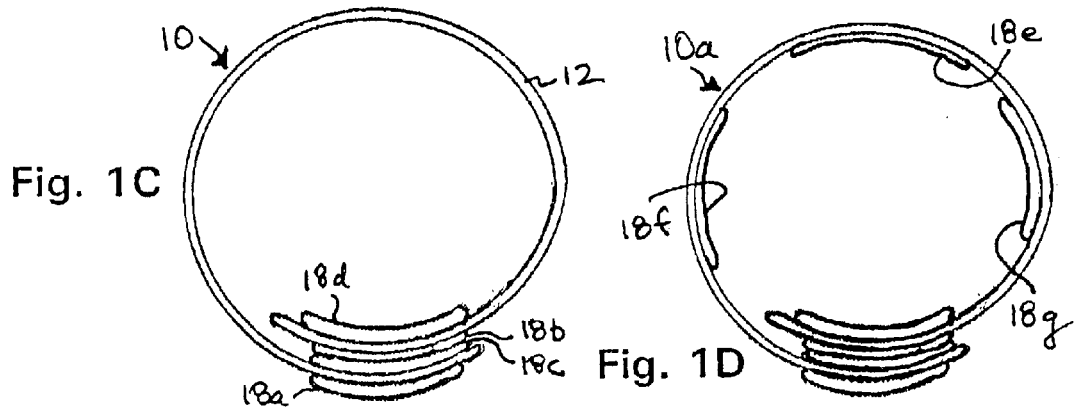
FIGS. 1C and 1D are side views of devices according to the present invention.

FIGS. 1A–1C show a device 10 according to the present invention which has a body 12, a top side 14 and a bottom side 16. At each end of the body 12 are amounts 18a, 18b, 18c, 18d of releasably cooperating fastener material which, in one particular aspect, are the well-known hook-and-loop types of VELCRO (tm) releasably cooperating fastener material material.

The amounts 18a and 18c are, in one aspect, of the known "softer" type of releasably cooperating fastener material material and the amounts 18b and 18d are of the known "stiffer" type of such material. As is well known, pressing the two types of material together provides a releasable connection between them. The releasably cooperating fastener material material may be connected to the body 2 with sewing, staples, rivets, and/or glue or a suitable adhesive.

Figure 2A:
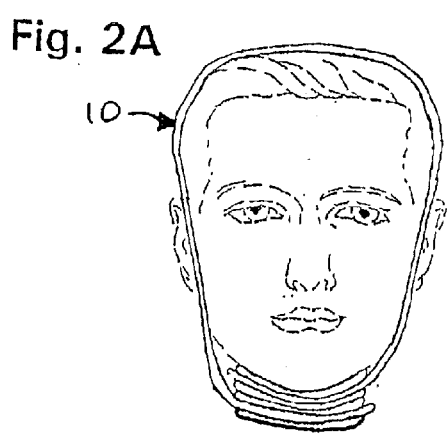
FIGS. 2A (from view) and 2B (side view) show a device according to the present invention in place on a person.
Figure 2B:
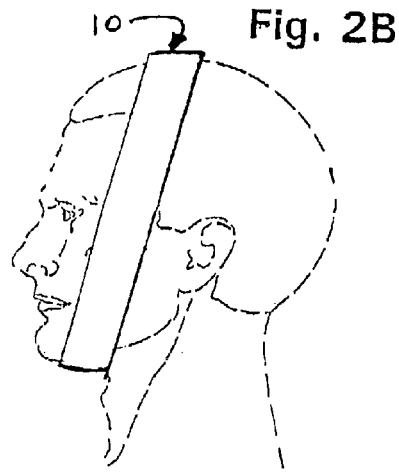

As shown in FIG. 1C, the ends of the body 12 have been wrapped onto themselves with areas of releasably cooperating fastener material material mating to hold the ends together. FIGS. 2A and 2B illustrate an embodiment of the device 10 in place around a person's head and chin. An amount of the "softer" releasably cooperating fastener material 18d abuts the person's chin. Alternatively, the device may be positioned with the amounts of material 18a–18d on top of the person's head or one side of the head.

FIG. 1D shows an embodiment 10a of the device of FIG. 1A which is like the device 10, but which has amount 18e of releasably cooperating fastener material which is positioned to cooperate with and interlock with a person's hair to assist in maintaining a desired position of the device with respect to the person's head and chin; and amounts 18f and 18g of the softer type of releasably cooperating fastener material or of padding or cushion material, e.g. to abut a person's ears or cheeks.

In one particular aspect a device like the device 10 according to the present invention is generally rectangular and is about three inches wide and about thirty inches long, made of stretchable elastic material (such as LYCRA™ or SPANDEX™). The amounts of releasably cooperating fastener material are about two inches wide and seven inches long and are sewn onto the body. In one particular aspect a stretch elastic material which is 67% polyester and 33% rubber sold under the trademark "STRETCH RITE HEAVY STRETCH ELASTIC" is used.

Figure 3:
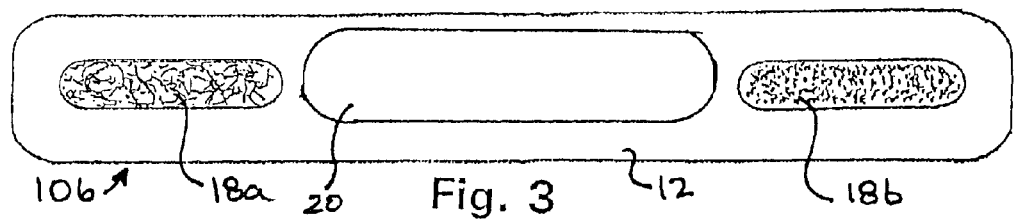
FIG. 3 is a top view of a device according to the present invention.

FIG. 3 shows a device 10b, like the device 10, FIG. 1A, and like numerals indicate like parts. Attached to the body 12 is a pad 20 which may be positioned so that when the device 10 is in place on a person the pad 20 pads or cushions a selected area or areas on the person's face, chin, head, arm, etc. It is within the scope of this invention to use multiple pads or cushions (like the pad 20) on the body 12 (or the body of any device according to the present invention).

Figure 4A:
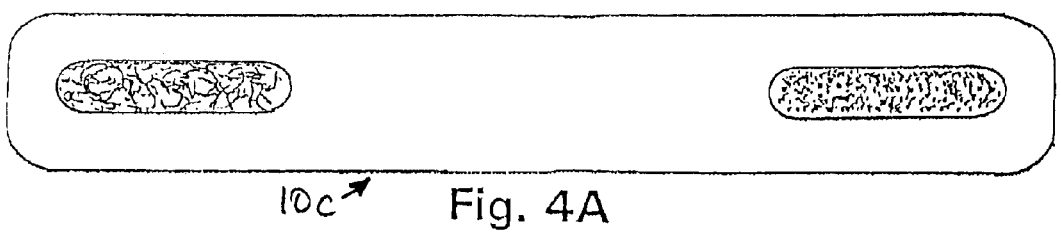
FIGS. 4A and 4B are top views of a device according to the present invention.
Figure 4B:
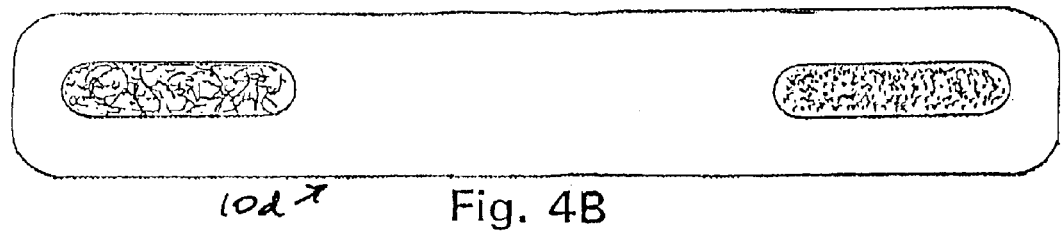
Figures 4C, 4D, 4E:
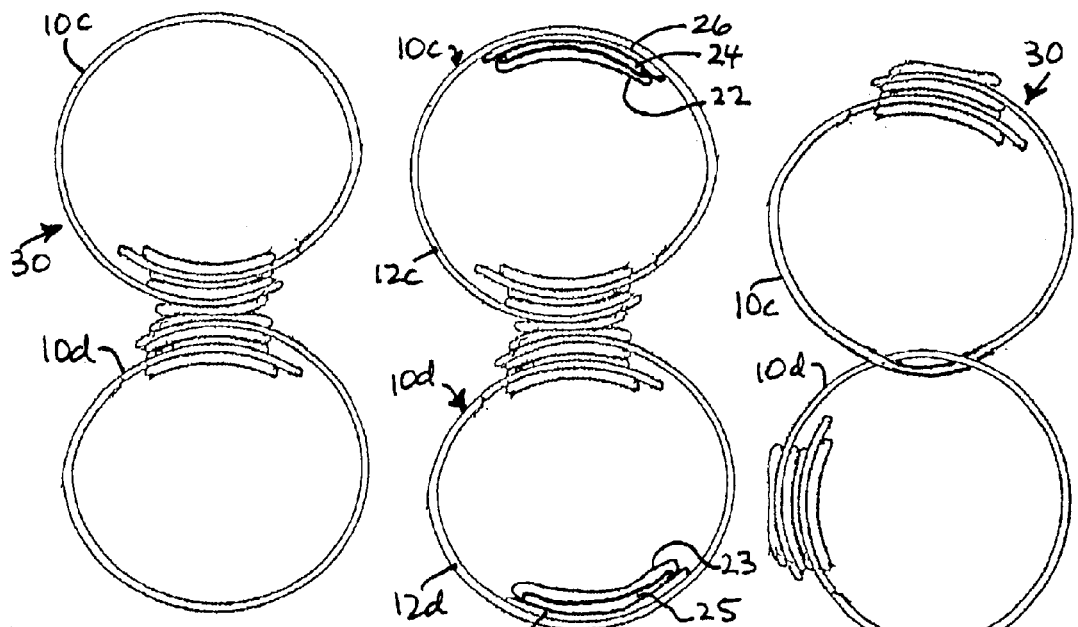
FIGS. 4C, 4D and 4E are side views of devices according to the present invention.

FIGS. 4A–4C illustrate the combination of two devices 10 to form a sling 30 in which an upper device 10 is releasably emplaceable around a person's neck and a lower device 10c is releasably emplaceable around a person's arm or hand. Releasably cooperating fastener material on the upper device 10d interlocks with corresponding releasably cooperating fastener material on the lower device 10 to hold the two devices together. Any two devices according to the present invention may be combined as shown in FIGS. 4C–4E.

As shown in FIG. 4D a cushion 22 is releasably attached to the device 10c with releasably cooperating fastener material 24 on the cushion 22 and releasably cooperating fastener material 26 on a body 12c (like the body 12, FIG. 1A) of the device 10c; and a cushion 23 is releasably attached to the device 10d with releasably cooperating fastener material 25 on the cushion 23 and releasably cooperating fastener material 27 on a body 12d (like the body 12, FIG. 1A) of the device 10d. Any device according to the present invention may have one or more cushions or pads connected in this manner to its body.

FIG. 4E shows another embodiment of the sling 30 in which a loop formed by the device 10c passes through a loop formed by the device 10d. Any two devices according to the present invention may be thus interconnected.

The present invention, therefore, in at least certain and not necessarily all, aspects discloses a device for releasable emplacement around a part of an animal's body, the device including at least one body member made of flexible material and having a length and a width and two spaced-apart ends including a first end and a second end and a top side and a bottom side, a first amount of releasably cooperating fastener material on the first end on the top side of the at least one body member, a second amount of releasably cooperating fastener material on the second end on the top side of the at least one body member, a third amount of releasably cooperating fastener material on the first end on the bottom side of the at least one body member, a fourth amount of releasably cooperating fastener material on the second end on the bottom side of the at least one body member, and the amounts of releasably cooperating fastener material positioned so that the first amount can releasably cooperate with the fourth amount upon folding the body member so that the ends are adjacent each other and the second amount can releasbly cooperate with the third amount upon folding the body member so that the ends are adjacent each other. Such a device may have one or some, in any possible combination, of the following: wherein the at least one body member has an amount of releasably cooperating fastener material positioned for releasably cooperating with hair of a person to facilitate maintenance of the device at a desired location on the animal's body; wherein one of the first, second, third, and fourth amounts of releasably cooperating fastener material is positionable to act as a cushion for a part of the animal's body; at least one cushion on the at least one body member for cushioning a part of the animal's body; wherein the at least one cushion is removably attached to the at least one body member; wherein the amounts of releasably cooperating fastener material are positioned so that the device can be emplaced tightly around an animal's head; wherein the device can be emplaced around an animal's head to inhibit activity from the group consisting of snoring, biting, and/or teeth grinding; wherein the at least one body member is two interconnected body members; wherein one of the body members is looped through the other; wherein releasably cooperating fastener material on one of the body members is releasably connected to releasably cooperating fastener material on the other body member; wherein the two body members is a first body member and a second body member, the first body member sized for emplacement over a shoulder of an animal and the second body member sized for emplacement around part of an arm of the animal; wherein each body member has at least one cushion for cushioning part of the animal in contact with the device; and/or wherein the animal's body is the body of a human being.

The present invention, therefore, in at least certain and not necessarily all, aspects discloses a method for inhibiting bodily activity of an animal, the bodily activity including, but not limited to, those from the group consisting of moving a mouth or jaw, biting, snoring, and teeth grinding, the method including emplacing a device around a head of the animal, the device as any disclosed herein according to the present invention, the device positioned with part of at least one body member over a head of the animal and part of the at least one body member under a chin of the animal. Such a method may include one or some, in any possible combination, of the following: wherein the animal is a human being; wherein; wherein the device includes at least one cushion on the at least one body member, and the method includes positioning the at least one cushion to contact a selected part of the head of the animal; and/or contacting hair on the head of the animal with at least one of the amounts of releasably cooperating fastener material on the at least one body.

The present invention, therefore, in at least certain and not necessarily all, aspects discloses a method for supporting a limb of an animal or an arm of an animal, the method including emplacing a device around parts of the animal's body, the device as any disclosed herein according to the present invention with two body members, emplacing the first body member over a shoulder of the animal or around part of its body, and emplacing the second body member around part of the arm of the animal or other of its limbs. Such a method may include one or both of the following: wherein the animal is a human being; and/or wherein the device has at least one cushion on the at least one body member, the method further including positioning the at least one cushion in contact with a part of the animal's body.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. Any patent or patent application referred to herein is incorporated fully herein for all purposes. The invention claimed herein is new and novel in accordance with 35 U.S.C. § 102 and satisfies the conditions for patentability in § 102. The invention claimed herein is not obvious in accordance with 35 U.S.C. § 103 and satisfies the conditions for patentability in § 103. This specification and the claims that follow are in accordance with all of the requirements of 35 U.S.C. § 112. The inventors may rely on the Doctrine of Equivalents to determine and assess the scope of their invention and of the claims that follow as they may pertain to apparatus not materially departing from, but outside of, the literal scope of the invention as set forth in the following claims. All patents referred to herein are incorporated fully herein for all purposes.

What is claimed is:

1. A method for supporting an arm of an animal, the method comprising emplacing a device around parts of the animal's body, the device comprising at least one body member made of flexible material and having a length and a width and two spaced-apart ends including a first end and a second end and a top side and a bottom side, a first amount of releasably cooperating fastener material on the first end on the top side of the at least one body member, a second amount of releasably cooperating fastener material on the second end on the top side of the at least one body member, a third amount of releasably cooperating fastener material on the first end on the bottom side of the at least one body member, a fourth amount of releasably cooperating fastener material on the second end on the bottom side of the at least one body member, and the amounts of releasably cooperating fastener material positioned so that the first amount can releasably cooperate with the fourth amount upon folding the body member so that the ends are adjacent each other and the second amount can releasbly cooperate with the third amount upon folding the body member so that the ends are adjacent each other, wherein the at least one body member is two interconnected body members, and wherein the two body members comprise a first body member and a second body member, the first body member sized for emplacement over a shoulder of an animal and the second body member sized for emplacement around part of a limb of the animal, emplacing the first body member over part of the animal, and emplacing the second body member around part of the limb of the animal.

2. The method of claim 1 wherein the animal is a human being and the limb is an arm of the human being.

3. The method of claim 1 wherein the device has at least one cushion on the at least one body member, the method further comprising positioning the at least one cushion in contact with a part of the animal's body.

4. A device for releasable emplacement around a part of an animal's body, the device comprising at least one body member made of flexible material and having a length and a width and two spaced-apart ends including a first end and a second end and a top side and a bottom side, a first amount of releasably cooperating fastener material on the first end on the top side of the at least one body member, a second amount of releasably cooperating fastener material on the second end on the top side of the at least one body member, a third amount of releasably cooperating fastener material on the first end on the bottom side of the at least one body member, a fourth amount of releasably cooperating fastener material on the second end on the bottom side of the at least one body member, the amounts of releasably cooperating fastener material positioned so that the first amount can releasably cooperate with the fourth amount upon folding the body member so that the ends are adjacent each other and the second amount can releasbly cooperate with the third amount upon folding the body member so that the ends are adjacent each other, and wherein the at least one body member is two interconnected body members, and wherein one of the body members is looped through the other.

5. The device of claim 4 wherein the at least one body member has an amount of releasably cooperating fastener material positioned for releasably cooperating with hair of the animal to facilitate maintenance of the device at a desired location on the animal's body.

6. The device of claim 4 wherein one of the first, second, third, and fourth amounts of releasably cooperating fastener material is positionable to act as a cushion for a part of the animal's body.

7. The device of claim 4 further comprising
at least one cushion on the at least one body member for cushioning a part of the animal's body.

8. The device of claim 7 wherein the at least one cushion is removably attached to the at least one body member.

9. The device of claim 4 wherein the amounts of releasably cooperating fastener material are positioned so that the device can be emplaced tightly around an animal's head.

10. The device of claim 9 wherein the device can be emplaced around an animal's head to inhibit activity from the group consisting of snoring, biting, and teeth grinding.

11. The device of claim 4 wherein releasably cooperating fastener material on one of the body members is releasably connected to releasably cooperating fastener material on the other body member.

12. The device of claim 4 wherein the two body members comprise a first body member and a second body member, the first body member sized for emplacement over a shoulder of an animal and the second body member sized for emplacement around part of an arm of the animal.

13. The device of claim 12 wherein each body member has at least one cushion for cushioning part of the animal in contact with the device.

14. The device of claim 4 wherein the animal's body is the body of a human being.

* * * * *